(12) United States Patent
Watkins

(10) Patent No.: US 6,533,745 B1
(45) Date of Patent: Mar. 18, 2003

(54) SUPPORT RELIEF HOSIERY

(76) Inventor: Lottie Mae Watkins, 110 N. State St., Raleigh, NC (US) 27601

( * ) Notice: Subject to any disclaimer, the term of this patent is extended or adjusted under 35 U.S.C. 154(b) by 0 days.

(21) Appl. No.: 09/558,262

(22) Filed: Apr. 25, 2000

Related U.S. Application Data

(60) Provisional application No. 60/131,511, filed on Apr. 29, 1999.

(51) Int. Cl.[7] .................................. A61F 13/00
(52) U.S. Cl. .............................. 602/60; 602/60; 602/62; 602/63
(58) Field of Search ................. 128/869, 882; 602/23, 26, 60–63, 66

(56) References Cited

U.S. PATENT DOCUMENTS

| | | | | |
|---|---|---|---|---|
| 255,180 A | * | 3/1882 | Master | 602/63 |
| 366,590 A | * | 7/1887 | Lubin | 602/63 |
| 967,585 A | * | 8/1910 | Teufel | 602/63 |
| 2,574,873 A | * | 11/1951 | Jobst | 602/63 |

* cited by examiner

*Primary Examiner*—Michael A. Brown

(57) ABSTRACT

The invention, Support Relief Hosiery shall be made in a variety of colors to appeal to the various users. An alternative sport model can be made In a variety of colors. There would be an additional area of support around the knee. The invention would be slipped over the foot and positioned on the leg where the support is needed the greatest. Pants can be worn over the invention without any obvious bulges or bumps. Adults as well as children of all ages can wear the hosiery if extra supports are needed. Many women wear support panty hose, but would rather have additional support just around the knees that would be provided by the hosiery. The relief hosiery does not fit the foot to cover the toes, but could be placed at the calf and pulled to lower thigh, then a sock may be worn at the individual's discretion.

1 Claim, 7 Drawing Sheets

SUPPORT RELIEF HOSIERY

This application claim benefit to U.S. Provisional application Ser. No. 60/131,511, filed Apr. 29, 1999.

FIELD OF THE INVENTION

A support relief hosiery to aid in the support of the knee and leg area.

BACKGROUND OF THE INVENTION

Support relief hosiery is special design leg hosiery for men, women and children to aid in the support of the knee and leg area. Many adults and children are trouble with weak knee joints and have severe aches in the area, especially if having to stand or be on their feet for long period of time. The Support Relief Hosiery product will.relieve this aching problem through the use of tightly support knit nylon over the lower thigh, knee and upper leg area. This relief hosiery utilizes stretch band overlapping with four (4) snaps at both the top of the lower thigh and bottom of the upper calf for adjustment for proper fitting. The stretch band overlapping at the tip of the lower thigh has four (4) snaps and the stretch band at the bottom of the upper calf can be made with four (4) snaps or without snaps. The nylon knit relief hosiery shall utilize brightly colored elastic band at the tip of the lower thigh and bottom of the upper calf of the relief hosiery with print for sport, hunters, etc. The relief hosiery would reach approximately three (3) inches above the knee and two (2) inches below the calf of the leg. The elastic band would be approximately two inches in width at the low part of the upper calf and three inches above the lower thigh. The relief hosiery is yet relatively simple based upon my review of the materials, it is my tentative conclusion that this product can take place with current, conventional an commercially available materials, using existing production technology. This innovation could us standard production technology. New research in this area may occur, but it doesn't appear required, nor does major restoring or exotic materials expense.

In this context, several prior inventors have been directed to this particular leg problem, some of, which are the subject of, issued United States patents. In particular, U.S. Pat. No. 4,027,667 to Roger Swallow and John E. Pendergrass for Therapeutic stockings. U.S. Pat. No. 4,176,665 to George I. Terpening, for stocking Knee Brace, U.S. Pat. No. 4,282,728 to Robert H. Tapp and Clarence W. Wall for Knee Protective Stocking. All deal with aspects of this knee and leg problem.

The present invention as disclosed below provides novel Support Relief Hosiery to aid in the process of relieving knee and upper leg discomfort.

SUMMARY OF THE INVENTION

The Support Relief Hosiery is designed to help relieve aching knees providing support to them. The relief hosiery shall surround the knee, lower thigh and the upper calf areas gently, but firmly, It will be particularly useful to elderly men and women who often suffer from the knee weakness. An alternative sport model in a variety of colors. Adults and children of all ages in many of approximately 98.4 million households in the United States and many others can use the hosiery elsewhere. The Support Relief Hosiery will provide a lasting massage to the area while being worn.

DETAILED DESCRIPTION OF THE INVENTION

Figure 1:
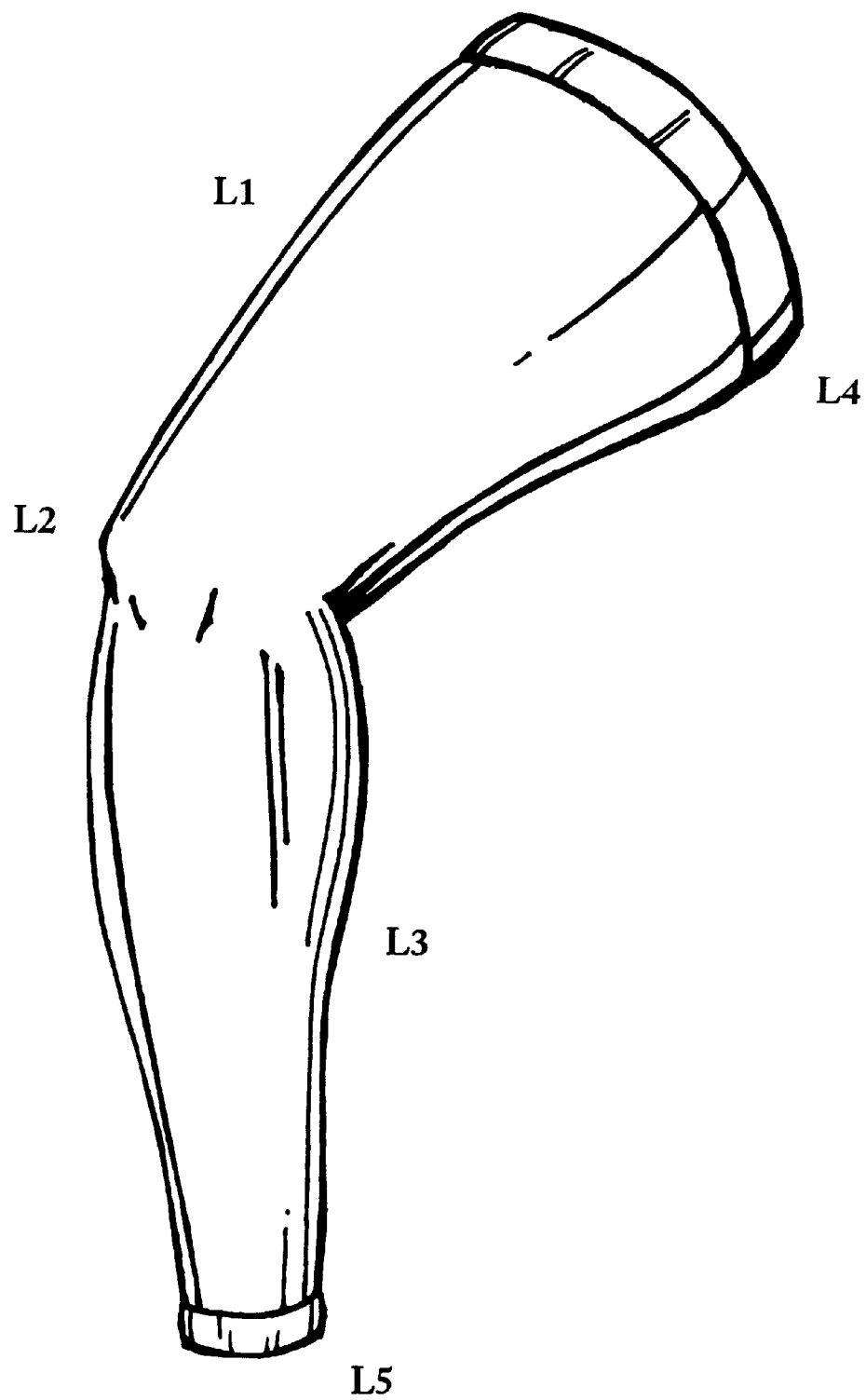
FIG. 1 is a perspective view of the Support Relief Hosiery.
Figure 2:
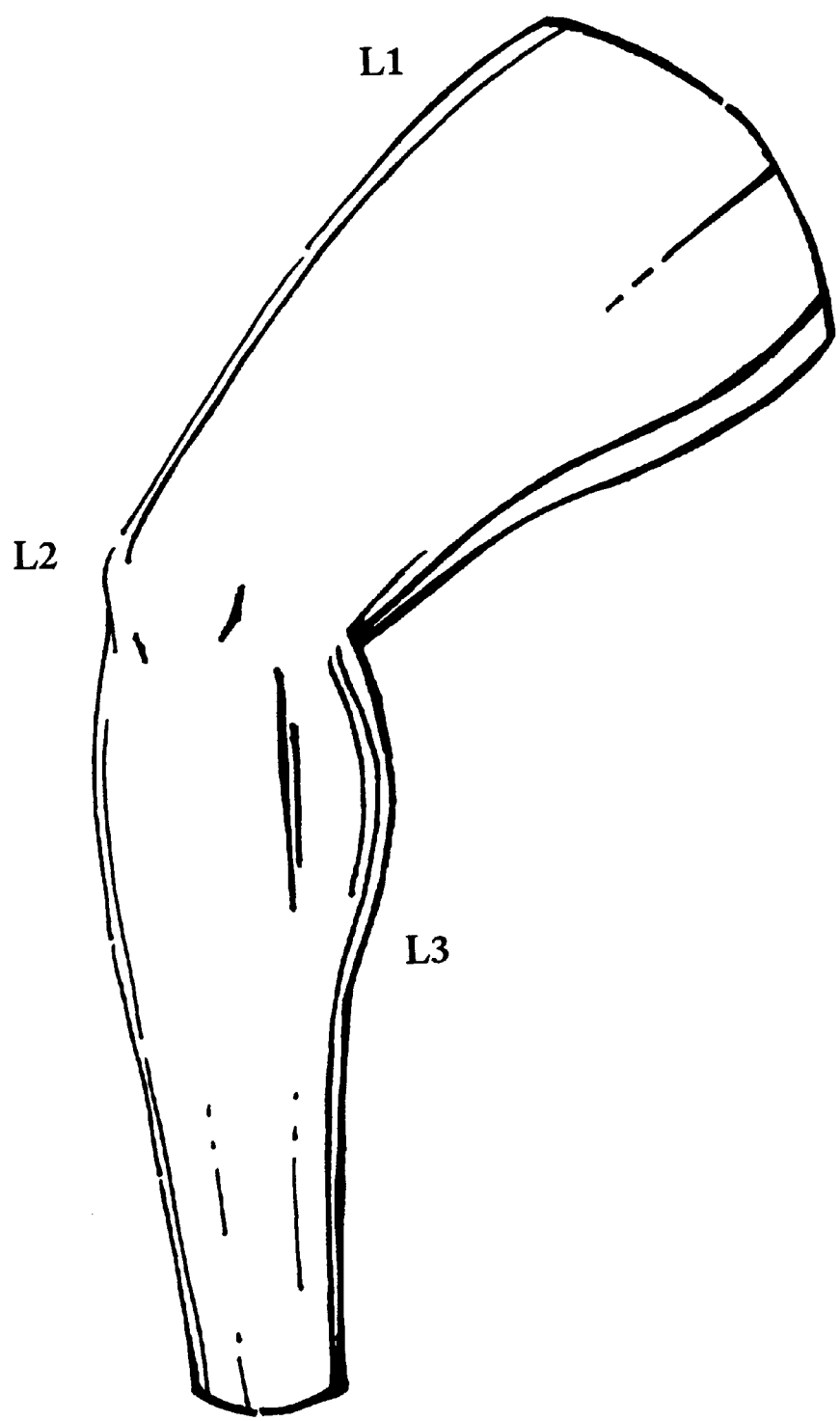
FIG. 2 is a perspective view of the length of the Support Relief Hosiery.
Figure 3:
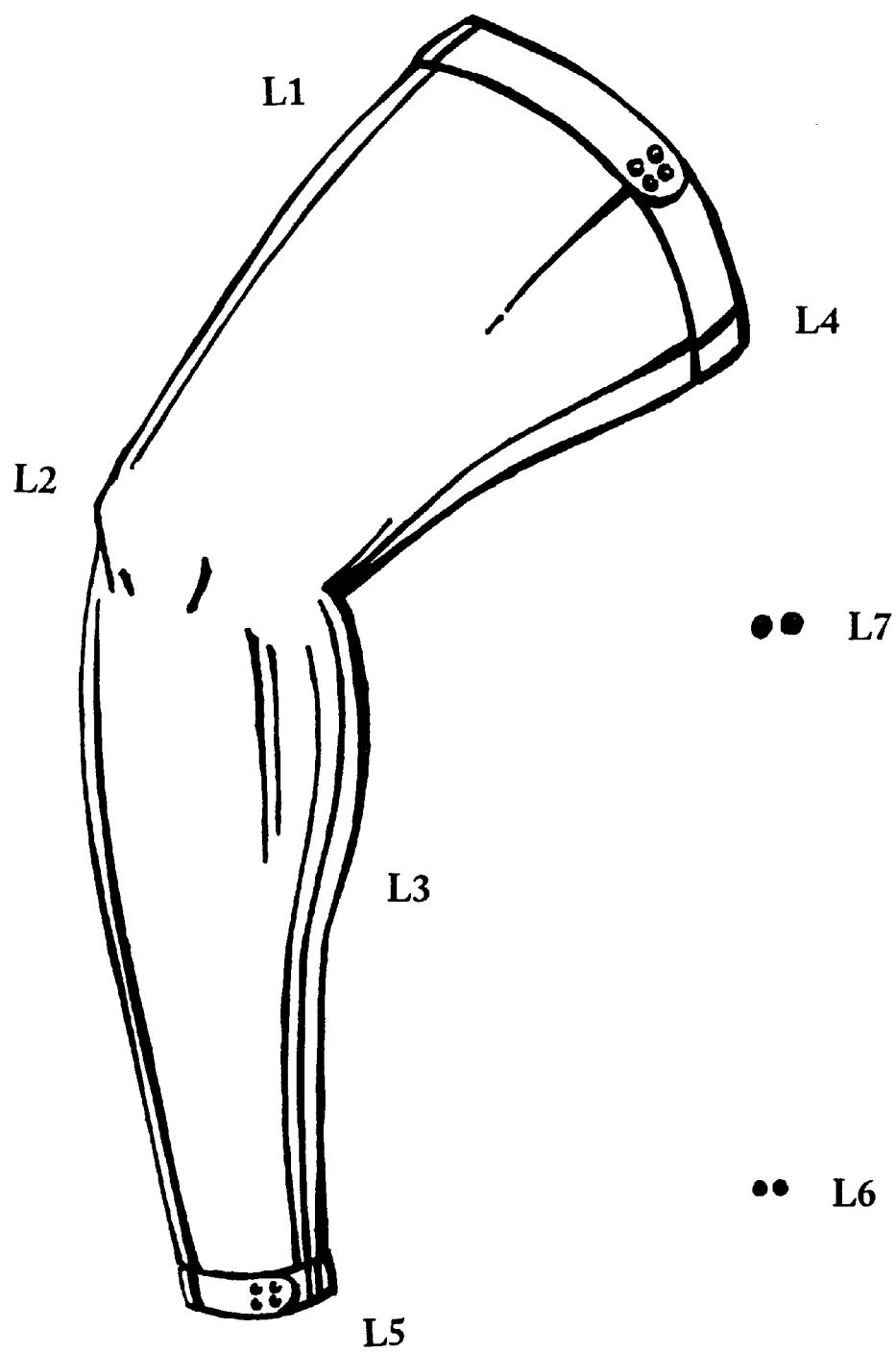
FIG. 3 is a perspective view of the relief hosiery with snaps attached.
Figure 4:
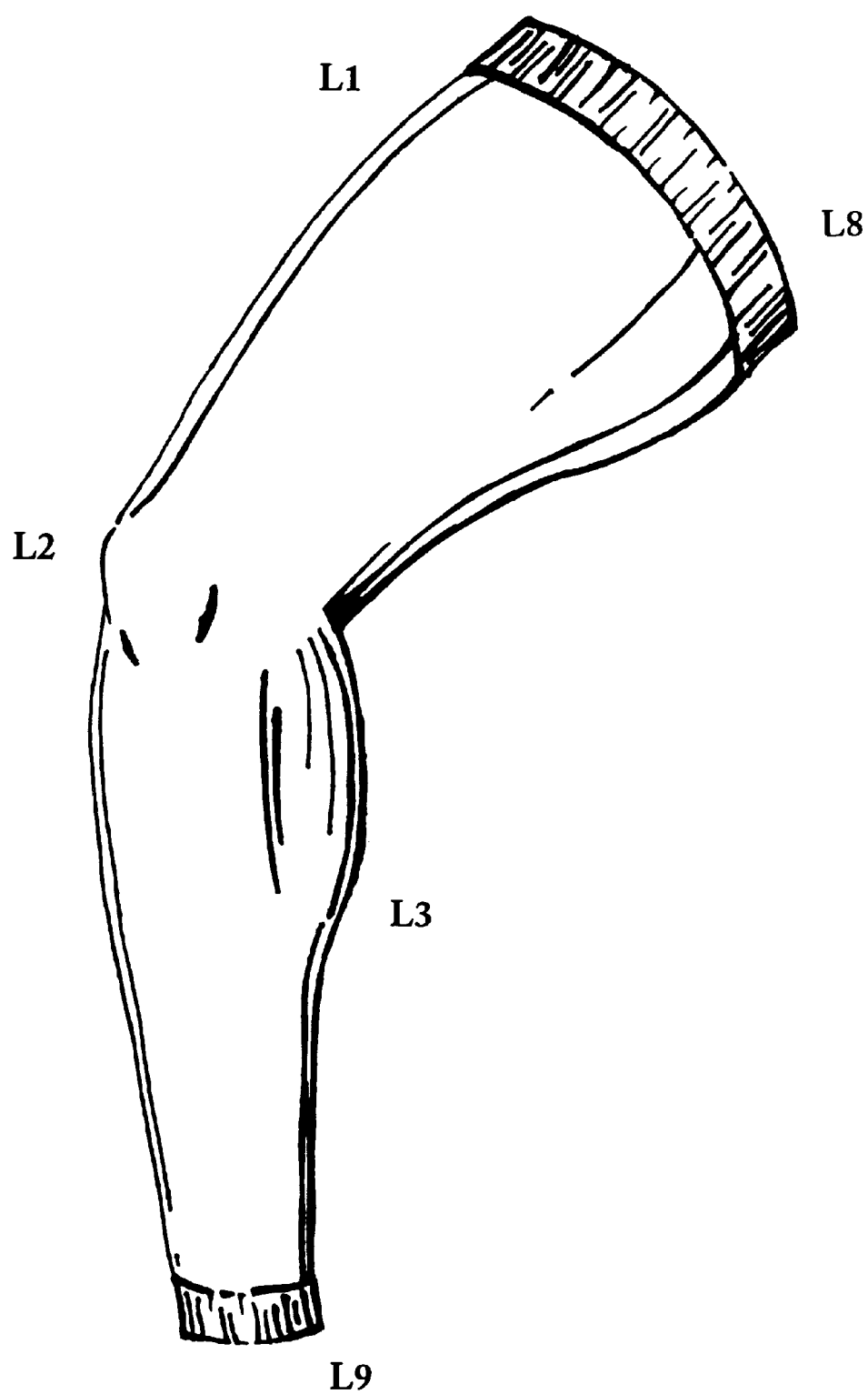
FIG. 4 is a perspective view of the relief hosiery with elastic band.

Referring to FIGS. 1–7 there is shown the Support Relief Hosiery of the invention, generally designated as L1 Relief Hosiery is made of support hosiery material that fit the leg snugly so as to create a supportive compressive, hosiery, FIG. 2, the L1 relief hosiery is twenty four (24) inches and/or in length according to the leg length of the individual. FIG, the upper and lower opening of the L1 relief hosiery is surrounded with L4 and L5 stretch bands are made into the material. The L1 relief hosiery L4 and L5 stretch bands are made double for strength and are made adjustable in diameter with L6 and L7, a set of snaps that are attached to L4 and L5, stretch bands. L6 snaps, size 3A are with L5 stretch band overlaps at the bottom secured by a suitable mean such as a hem stitch with four (4) L6 snaps for adjustment.

FIGS. 4–7, the upper and lower openings are surrounded with L8 and L9 an elastic band having a corrugated inner surface.

Figure 5:
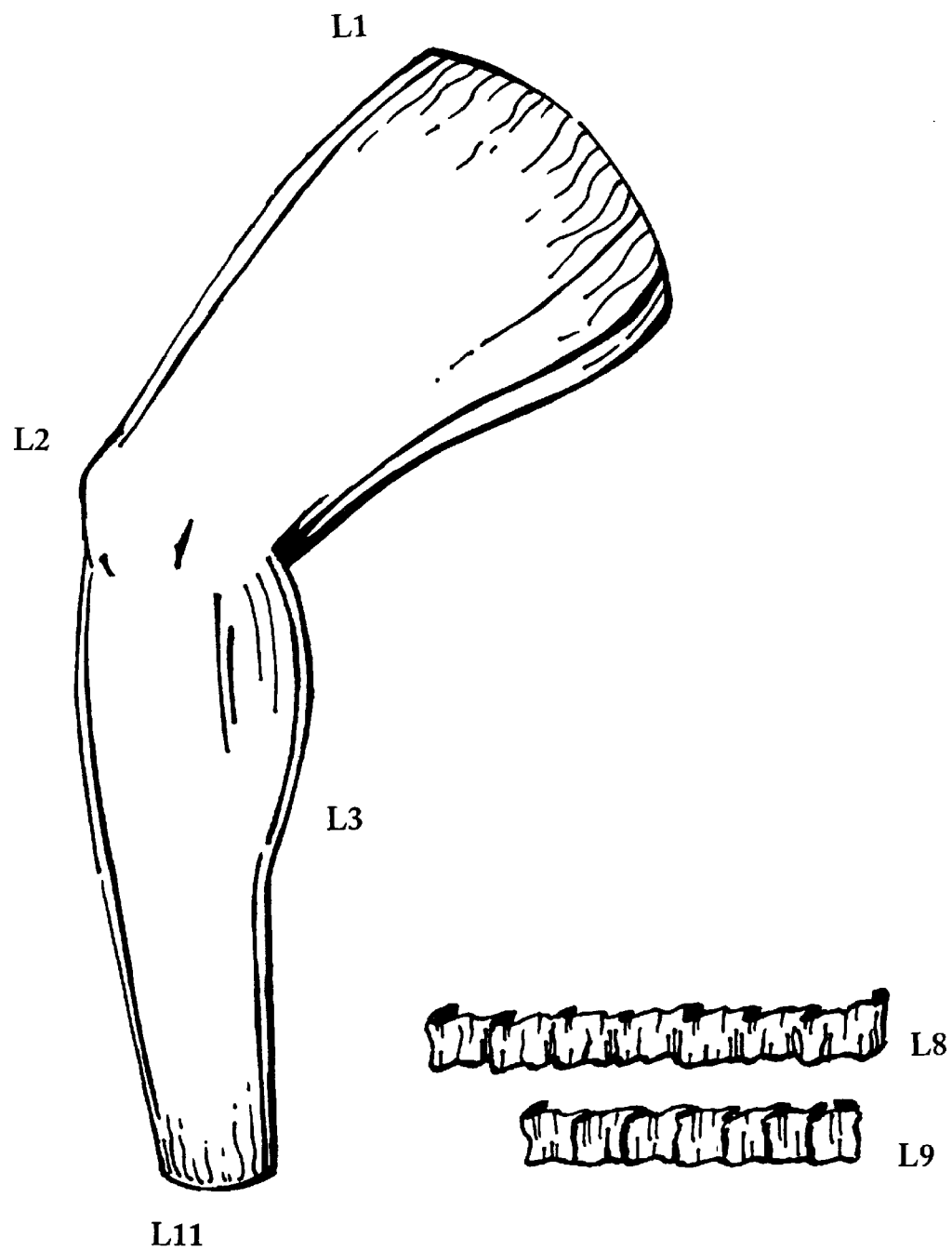
FIG. 5 is a perspective view of the relief hosiery showing the length before the elastic bands are attached.
Figure 6:
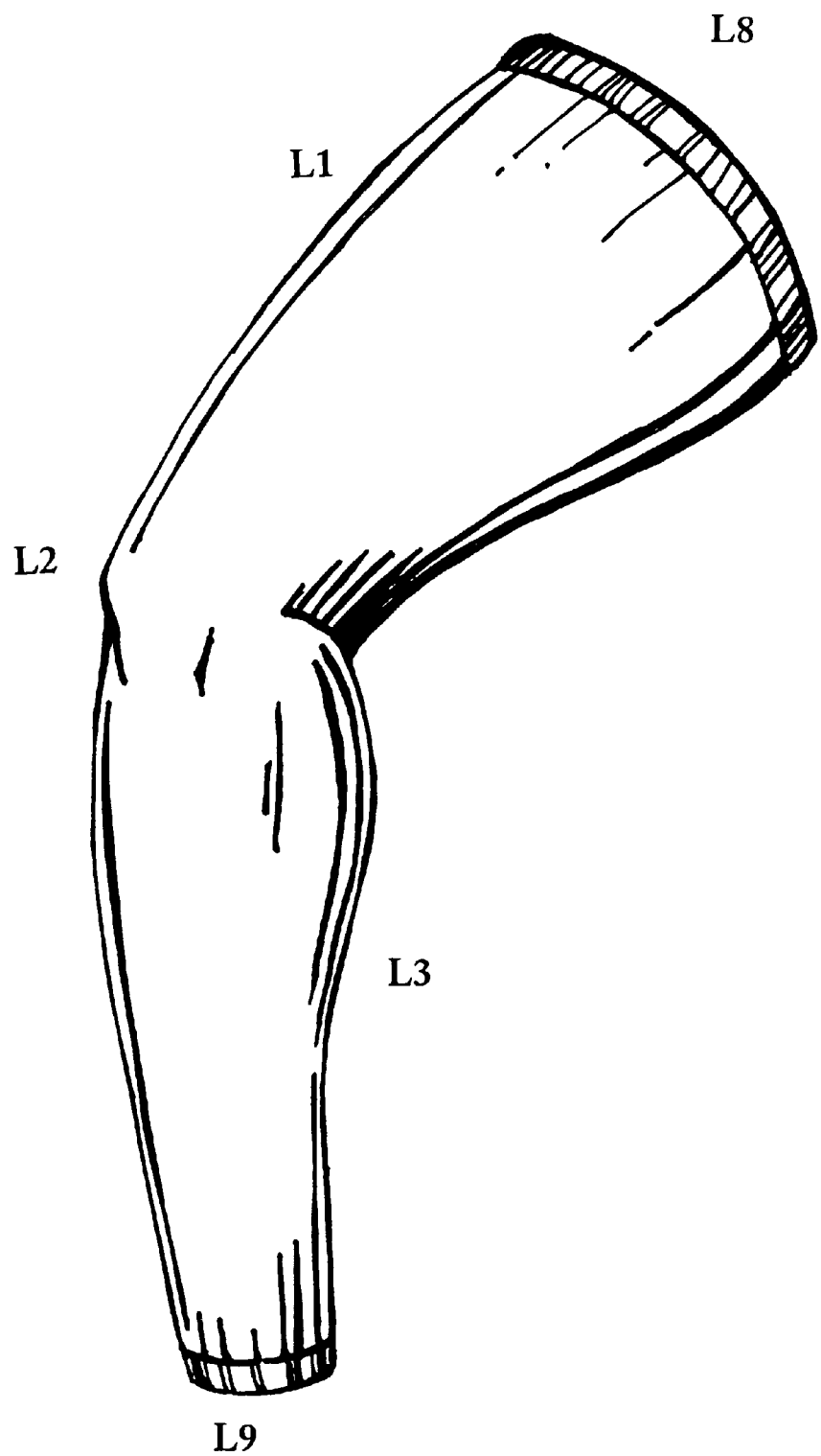
FIG. 6 is a perspective view of the nylon knit relief hosiery the side view of the hosiery.
Figure 7:
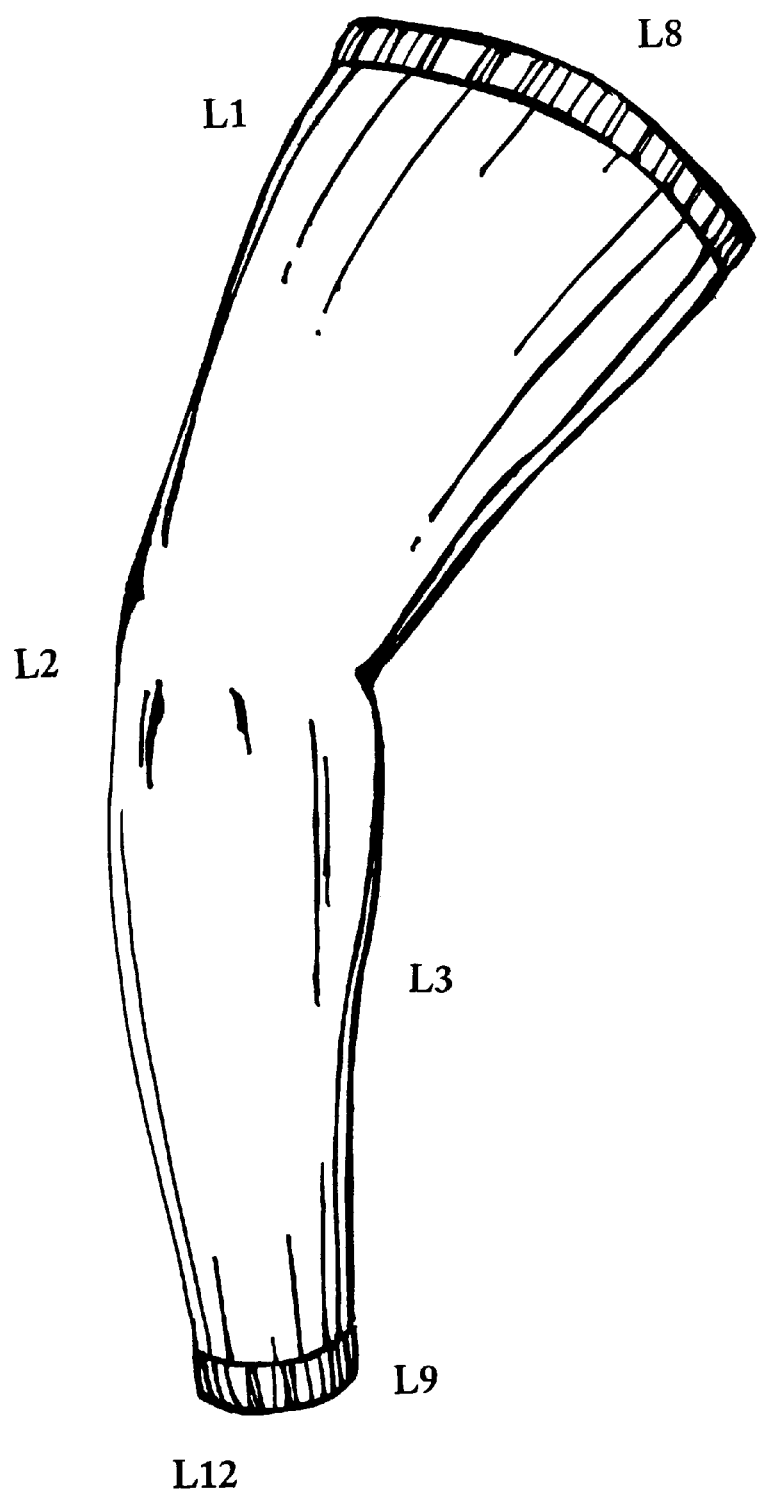
FIG. 7 is a perspective view showing the knee of the relief hosiery.

FIG. 5, L8 and L9 elastic band secured by suitable means such stitching L8 elastic band to top of the lower thigh of L1 relief hosiery and L9 elastic band is stitched to bottom the upper calf of L1 relief hosiery. FIG. 6, L2 and L3 demonstrate how the L1 relief hosiery will fit over the calf and knee. FIG. 7, L1 relief hosiery is three (3) inches in width above the lower thigh. L9 elastic band is tow (2) inches in width at L12 below the upper calf.

What I claim as my invention is:

1. A support relief hosiery for aiding in the support of the knee and leg area comprising a nylon knit tubular hosiery having a top and a bottom, a first stretch band attached at the top of said tubular hosiery, said first elastic band having four snaps attached thereto, a second stretch band attached at the bottom of said tubular hosiery, said second band having four snaps attached thereto, said first stretch band is adapted to fit snugly against a lower thigh, said second stretch band is adapted to fit snugly against the calf to create a compression around the leg, wherein said first and second elastic bands having inner surfaces that are corrugated.

* * * * *